(12) United States Patent
Kim et al.

(10) Patent No.: US 9,527,824 B2
(45) Date of Patent: Dec. 27, 2016

(54) PHARMACEUTICAL COMPOSITION FOR PREVENTING OR TREATING COGNITIVE IMPAIRMENT-RELATED DISEASE COMPRISING MORPHOLINE OR PIPERAZINE BASED COMPOUNDS, AND DONEPEZIL

(71) Applicant: KOREA INSTITUTE OF SCIENCE AND TECHNOLOGY, Seoul (KR)

(72) Inventors: Dong Jin Kim, Seoul (KR); Young Soo Kim, Yongin-si (KR); Hye Yun Kim, Seoul (KR); Hyun Jin Kim, Bucheon-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 32 days.

(21) Appl. No.: 14/316,963

(22) Filed: Jun. 27, 2014

(65) Prior Publication Data

US 2015/0005306 A1 Jan. 1, 2015

(30) Foreign Application Priority Data

Jun. 27, 2013 (KR) ........................ 10-2013-0074861

(51) Int. Cl.
| | |
|---|---|
| *A61K 31/535* | (2006.01) |
| *C07D 295/15* | (2006.01) |
| *A61K 31/495* | (2006.01) |
| *A61K 31/5375* | (2006.01) |
| *C07D 295/088* | (2006.01) |

(52) U.S. Cl.
CPC ........... *C07D 295/15* (2013.01); *A61K 31/495* (2013.01); *A61K 31/5375* (2013.01); *C07D 295/088* (2013.01)

(58) Field of Classification Search
None
See application file for complete search history.

(56) References Cited

U.S. PATENT DOCUMENTS

2011/0144111 A1    6/2011   Kim et al.

FOREIGN PATENT DOCUMENTS

| JP | 11-158143 A | 6/1999 |
|---|---|---|
| KR | 10-20050059164 A | 6/2005 |
| KR | 100937623 B1 | 1/2008 |
| WO | WO2005014563 A1 | 2/2005 |
| WO | 2005079789 A1 | 9/2005 |

OTHER PUBLICATIONS

Kim, H. et al Journal of Alzheimer's Disease, vol. 22, No. 1, pp. 73-85, 2010.*
Tokita, K. et al., Pharmacol. Biochem. Behav. 2002 vol. 73 pp. 511-519.*
Notice of Allowance dated on Dec. 1, 2014, corresponding Korean Patent Application No. 10-2013-0074861.
Geriater Med, 2011, pp. 809-812, vol. 49(7).
Communications of the extended European search report of the European patent application No. 14817212.5 issued on Oct. 6, 2016, which corresponds to this application.
Communications of Japanese Application No. 2016-523649 issued on Sep. 13 ,2016, which corresponds to this application.

* cited by examiner

*Primary Examiner* — Heidi Reese
(74) *Attorney, Agent, or Firm* — Goldilocks Zone IP Law

(57) ABSTRACT

Provided is a pharmaceutical composition for preventing or treating a cognitive impairment-related disease, the pharmaceutical composition including N-(2-hydroxyethyl)piperazine-N'(3-propane sulfonic acid), a pharmaceutically acceptable salt thereof or a derivative thereof, and donepezil, a pharmaceutically acceptable salt thereof or a derivative thereof. The composition may be used in preventing or treating a cognitive impairment-related disease.

3 Claims, 3 Drawing Sheets

PHARMACEUTICAL COMPOSITION FOR PREVENTING OR TREATING COGNITIVE IMPAIRMENT-RELATED DISEASE COMPRISING MORPHOLINE OR PIPERAZINE BASED COMPOUNDS, AND DONEPEZIL

RELATED APPLICATIONS

This application claims the benefit of Korean Patent Application No. 10-2013-0074861, filed on Jun. 27, 2013, in the Korean Intellectual Property Office, the disclosure of which is incorporated herein in its entirety by reference.

BACKGROUND

1. Field

One or more embodiments of the present invention relate to a pharmaceutical composition for preventing or treating cognitive impairment-related diseases and a method of preventing or treating cognitive impairment-related diseases by using the pharmaceutical composition.

2. Description of the Related Art

Dementia comprehensively encompass complex clinical symptoms from which a normally developed brain is impaired or destroyed by external factors such as trauma, diseases, or genetic factors, which leads to abnormal deterioration of overall cognitive functions and higher metal processes, such as language, learning, and intelligence. Dementia may be largely divided into dementia by Alzheimer's disease, vascular dementia, dementia by specific neural diseases, and systematic disease, etc. according to the cause of disease, and the dementia by Alzheimer's disease is responsible for 50% or more of them. Dementia by Alzheimer's disease progresses due to an accumulation of a β-amyloid protein that causes the dementia, into an oligomer form, fibril form, and then into a plaque form, during which process the brain including neuron cells are damaged.

Treatments that have been developed so far were based on the fact that a level of acetylcholine in the brain of an Alzheimer's disease dementia patient is lower than that of a normal person and thus, the treatments were developed to increase the level of acetylcholine in the brain or increase the activity of cholinergic neuron cells. Acetylcholine esterase is an enzyme that hydrolyzes acetylcholine into choline and acetate and thus, an acetylcholine esterase inhibitor is used as a treatment for Alzheimer's disease dementia. The dementia treatment may be donepezil (product name: ARICEPT), rivastigmin (product name: EXELON), and galantamine (product name: REMINYL). However, these drugs are not used to fundamentally treat the disease, but to relieve memory impairment. The drugs also showed side-effects during clinical trials and effects of the drugs decrease when they are used for a long period of time.

Meanwhile, a pharmaceutical composition including EPPS for preventing or treating diseases related to β-amyloid accumulation was disclosed in a research paper. In the research paper, N-(2-hydroxyethyl)piperazine-N'-(3-propane-sulfonic acid) (EPPS) inhibits the accumulation of β-amyloid fibrils or oligomers and decomposes the accumulated β-amyloid fibrils or oligomers to inhibit toxicity caused by the β-amyloid.

Accordingly, to effectively prevent and treat dementia, a drug that inhibits the accumulation of β-amyloid, which is a primary factor for dementia, and physiologically increases the amount of acetylcholine in the brain is needed.

SUMMARY

One or more embodiments of the present invention include a pharmaceutical composition for preventing or treating cognitive impairment-related diseases, the pharmaceutical composition including a morpholine compound or a piperazine compound, a pharmaceutically acceptable salt thereof, or a derivative thereof; and donepezil, a pharmaceutically acceptable salt thereof, or a derivative thereof.

One or more embodiments of the present invention include a method of preventing or treating cognitive impairment-related diseases using a morpholine compound or a piperazine compound, a pharmaceutically acceptable salt thereof, or a derivative thereof; and donepezil, a pharmaceutically acceptable salt thereof, or a derivative thereof.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
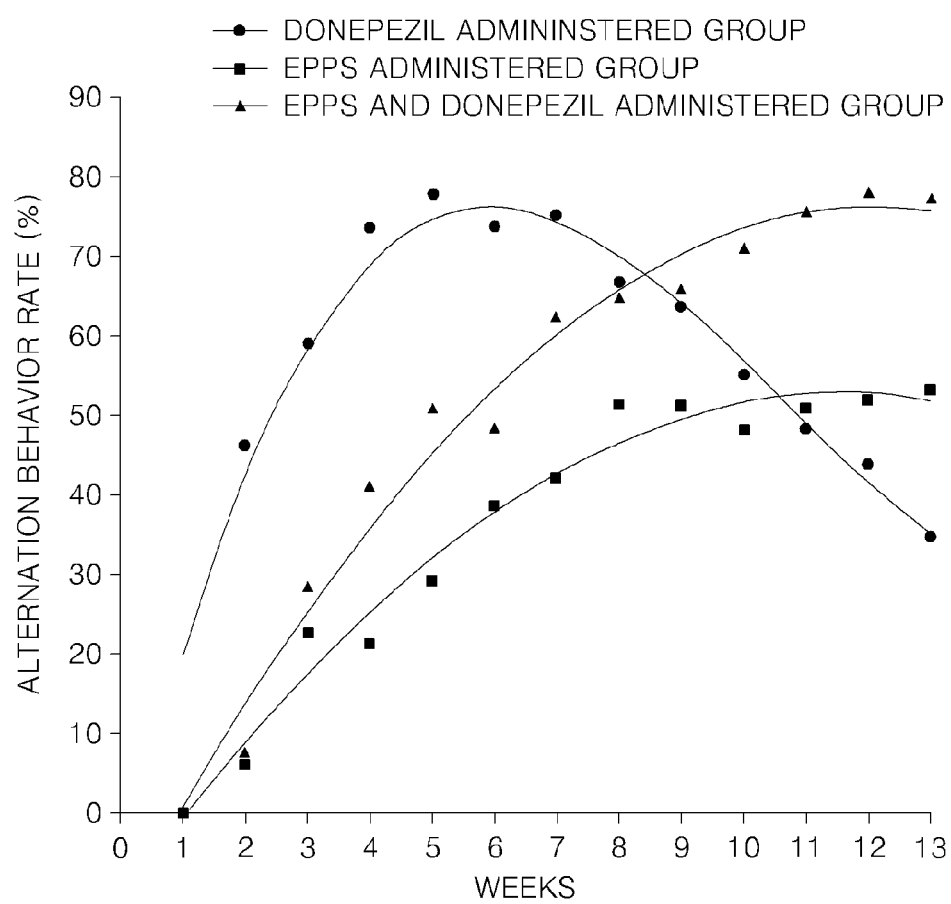
FIG. 1 shows experimental results of a Y-maze behavior test of an Alzheimer's disease transgenic mouse (●: donepezil administered group, ▲: EPPS and donepezil administered group, and ■: EPPS administered group)

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Provided is a pharmaceutical composition for preventing or treating cognitive impairment-related diseases, the pharmaceutical composition including a morpholine compound or a piperazine compound, a pharmaceutically acceptable salt thereof, or a derivative thereof; and donepezil, a pharmaceutically acceptable salt thereof, or a derivative thereof.

Provided is a method of preventing or treating cognitive impairment-related diseases using a morpholine compound or a piperazine compound, a pharmaceutically acceptable salt thereof, or a derivative thereof; and donepezil, a pharmaceutically acceptable salt thereof, or a derivative thereof.

Provided is a pharmaceutical composition for preventing or treating cognitive impairment-related diseases, including a morpholine compound or a piperazine compound represented by Formula 1 below and having a sulfonic acid structure or a carboxylic acid structure, a pharmaceutically acceptable salt thereof, or a derivative thereof; and donepezil, a pharmaceutically acceptable salt thereof, or a derivative thereof:

[Formula 1]

In Formula 1,
Z may be O or N;
when Z=O, $R^1$ is not bonded and when Z=N, $R^1$ may be —$(CH_2)_n$—OH; and
$R^2$ may be —$(CH_2)_n$—$R^3$,
n may be an integer of 1 to 5, and
$R^3$ may be —COON or —$SO_3H$.

In the pharmaceutical composition described above, the compound of Formula 1 may be selected from the group consisting of compounds represented by Formulae 1a to 1e.

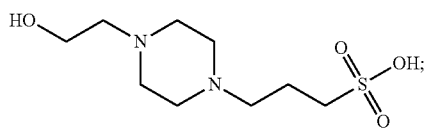
(Formula 1a)

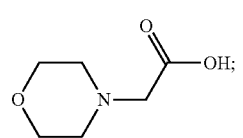
(Formula 1b)

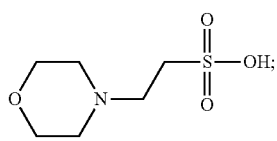
(Formula 1c)

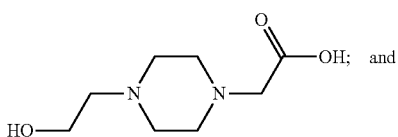
(Formula 1d)

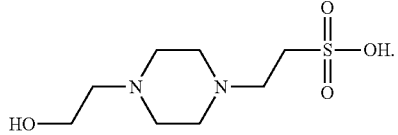
(Formula 1e)

Formula 1a is N-(2-hydroxyethyl)piperazine-N'(3-propane sulfonic acid) (EPPS).

In the pharmaceutical composition, donepezil is a compound having a chemical name of 1-benzyl-4-[(5,6-dimethoxy-indan-1-one)-2-yl]methyl piperazine. A hydrochloride salts of 1-benzyl-4-[(5,6-dimethoxy-indan-1-one)-2-yl] methyl piperazine, which is known as donepezil hydrochloride, is commercially available as a treatment for Alzheimer's disease named Aricept®.

The expression, "a pharmaceutically acceptable salt" refers to an inorganic and an organic acid addition salts. An acid addition salt may be obtained from an inorganic acid or a non-toxic organic acid. The inorganic acid may be hydrochloric acid, nitric acid, phosphoric acid, sulfuric acid, hydrobromic acid, hydroiodic acid, nitrous acid and phosphorous acid. The non-toxic organic acid may be oxalic acid, maleic acid, fumaric acid, malic acid, tartaric acid, citric acid, benzoic acid, aliphatic mono and dicarboxylate, phenyl-substituted alkanoate, hydroxy alkanoate and alkanedionate, aromatic acid, and aliphatic and aromatic sulfonic acid. A pharmaceutically non-toxic salt may be sulfate, pyrosulfate, bisulfate, sulfite, bisulfite, nitrate, phosphate, mono-hydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butene-1,4-dioate, hexane-1,6-dioate, benzoate, chlorobenzoate, methyl benzoate, dinitrobenzoate, hydroxybenzoate, methoxy benzoate, phthalate, terephthalate, benzene sulfonate, toluene sulfonate, chlorobenzene sulfonate, xylene sulfonate, phenyl acetate, phenyl propionate, phenyl butyrate, citrate, lactate, β-hydroxy-butyrate, glycolate, tartrate, methane sulfonate, propane-sulfonate, naphthalene-1-sulfonate, naphthalene-2-sulfonate or mandelate.

The expression "derivative" refers to a compound obtained from a substitution of a portion of the compound to another atom or an atomic group.

The cognitive impairment-related disease refers to a disease that induces cognitive impairment regardless of its fundamental cause. The cognitive impairment-related disease may be a mild cognitive impairment, a moderate cognitive impairment, or a severe cognitive impairment. The cognitive impairment-related disease may be dementia, Alzheimer's disease, amnesia, or Parkinson's disease. The dementia may be Alzheimer's disease dementia, senile dementia, or youth dementia. The Alzheimer's disease may be accompanied by behavioral and mental symptoms such as memory loss, poor language skills, poor spatiotemporal skills, poor judgment, and psychiatric behaviors such as depression, and physical symptoms such as urinary and fecal incontinence. The amnesia refers to memory impairment and may be induced by various diseases such as Alzheimer's disease, vascular dementia, epilepsy, and alcohol binging.

The term "prevention" refers to all actions that inhibit or delay the onset of disease through an administration of a composition. The term "treatment" refers to all actions in which symptoms of disease are relieved or advantageously changed due to the administration of a composition.

The morpholine compound or the piperazine compound represented by Formula 1 and including sulfonic acid structure or carboxylic acid structure a pharmaceutically acceptable salt thereof, or a derivative thereof; and donepezil, a pharmaceutically acceptable salt thereof, or a derivative thereof may be administered simultaneously or individually at different times. The components may be used as a conventional pharmaceutical formulation. Also, the components may be prepared as a single formulation or separate individual formulations.

The pharmaceutical composition may include a morpholine compound or a piperazine compound represented by Formula 1 and having sulfonic acid structure or a carboxylic acid structure, a pharmaceutically acceptable salt thereof, or a derivative thereof; and donepezil, a pharmaceutically acceptable salt thereof, or a derivative thereof, an amount of which may be about 0.0001 wt % to about 10 wt % or about 0.001 wt % to about 1 wt % based on a total weight of the entire composition. When the pharmaceutical composition is a single formulation, each component may be mixed at a proportion of about 0.0001 wt % to about 10 wt %. When the pharmaceutical composition is a complex formulation (mixed formulation), an amount of each component may be about 0.0001 wt % to about 10 wt % based on a sum of all components.

The pharmaceutical composition may be formulated as a formulation for oral administration or a formulation for parenteral administration.

In the pharmaceutical composition, a solid formulation for an oral administration may be a tablet, a pill, a light and soft capsule, a solution, a suspension, an emulsion, a syrup, granules, or an elixir. The solid formulation may further include a carrier. The carrier may be starch, calcium carbonate, sucrose, lactose, or gelatin. Also, the solid formulation may further include a lubricant such as magnesium stearate or talc. In the pharmaceutical composition, a liquid formulation for oral administration may be a suspension, a liquid formulation, an emulsion, or a syrup. The liquid formulation may include water or liquid paraffin. The liquid formulation may include an excipient, for example, a wetting agent, a sweetener, an aromatic, or a preservative.

In the pharmaceutical composition, the formulation for parenteral administration may be a sterilized aqueous solution, a water-insoluble excipient, a suspension, an emulsion, a lyophilized powder, a suppository, or an inhalation. The water-insoluble excipient or the suspension may include vegetable oil or ester. The vegetable oil may be propylene glycol, polyethylene glycol, or olive oil. The ester may be ethylolate. A base of the suppository may be witepsol, macrogol, tween 61, cacao butter, laurinum, or glycerogelatin. The inhalant may be prepared by using an active compound in a powder or a liquid form, mixing the active compound in a propellant for inhalation and/or carrier, and then charging the compound obtained therefrom into a suitable vaporizer. When the active compound is a powder, a conventional powder vaporizer may be used and when the active compound is a liquid, a vaporizer such as a nebulizer may be used. Also, the inhalant may be selectively mixed with a conventional surfactant, oil, perfume, cyclodextrin or a derivative thereof.

The pharmaceutical composition may further include a carrier, an excipient, or a diluent. The carrier, the excipient, and the diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, or mineral oil.

A dose of the pharmaceutical composition may be suitably selected by a person in the art depending on physical state and weight, degree of disease, form of drug, route of administration, and duration. However, an amount of the EPPS may be about 0.0001 mg/weight kg to about 100 mg/weight kg or about 0.001 mg/weight kg to about 10 mg/weight kg, which may be administered once a day or many times a day. An amount of the donepezil may be about 0.0001 mg/weight kg to about 100 mg/weight kg or about 0.001 mg/weight kg to about 10 mg/weight kg, which may be administered once a day, many times a day, or once several days. The pharmaceutical composition may be administered to mammals including rats, mice, livestock, and humans through various routes. A method of administration may be oral, rectal, intravenous, intramuscular, subcutaneous, epidural, or intracerebroventricular injection.

The pharmaceutical composition may be prepared by using a pharmaceutically suitable and physiologically acceptable adjuvant, in addition to active ingredients and the adjuvant may be a solubilizer, such as an excipient, a disintegrating agent, a sweetener, a binder, a coating agent, a swelling agent, a lubricant, grease, or a flavoring agent. The pharmaceutical composition may be suitably formulated for administration by including one or more types of a pharmaceutically acceptable carrier, in addition to the active ingredients.

In the composition that may be formulated as liquid, a pharmaceutically acceptable carrier may be a mixture of two or more selected from saline solution, sterile water, Ringer's solution, buffered saline solution, albumin injection solution, dextrose solution, maltodextrin solution, glycerol, and ethanol, and another conventional additive such as an antioxidant, a buffer, a fungistat, or the like may be added depending on the need. Also, a diluents, a dispersant, a surfactant, a binder, and a lubricant may be added thereto to prepare the composition as a formulation for injection such as an aqueous solution, a suspension, and an emulsion, or as a pill, a pellet, a capsule, a granule, or a tablet. Furthermore, a method disclosed in Remington's Pharmaceutical Science, Mack Publishing Company, Easton Pa. may be used as a method suitable in the art to prepare formulations suitable for each disease or component.

A pharmaceutical formulation type of the pharmaceutical composition may be a granule, a powder, a coated tablet, a tablet, a capsule, a suppository, a syrup, a juice, a suspension, an emulsion, a drop, an injectable solution, or a sustained release formulation of active compounds.

Provided is a pharmaceutical composition for preventing or treating cognitive impairment-related diseases, the pharmaceutical composition including a morpholine compound or a piperazine compound represented by Formula 1 below and having a sulfonic acid structure or a carboxylic acid structure, a pharmaceutically acceptable salt thereof, or a derivative thereof; and donepezil, a pharmaceutically acceptable salt thereof, or a derivative thereof

[Formula 1]

In Formula 1,
Z may be O or N;
when Z=O, $R^1$ is not bonded and when Z=N, $R^1$ may be —$(CH_2)_n$—OH; and
$R^2$ may be —$(CH_2)_n$—$R^3$,
n may be an integer selected from 1 to 5, and
$R^3$ may be —COON or —$SO_3H$.

The EPPS, donepezil, a pharmaceutically acceptable salt thereof, and a derivative thereof, cognitive impairment-related diseases, prevention, and treatment are the same as described above.

The term "subject" refers to mammals including humans.

The morpholine compound or the piperazine compound represented by Formula 1 and having a sulfonic acid structure or a carboxylic acid structure, a pharmaceutically acceptable salt thereof, or a derivative thereof; and donepezil, a pharmaceutically acceptable salt thereof, or a derivative thereof may be simultaneously or sequentially administered to the subject.

A complex formulation including the morpholine compound or the piperazine compound represented by Formula 1 and having a sulfonic acid structure or a carboxylic acid structure, a pharmaceutically acceptable salt thereof, or a derivative thereof; and donepezil, a pharmaceutically acceptable salt thereof, or a derivative thereof may be simultaneously or sequentially administered to the subject may be administered to the subject. Also, a single formulation of the morpholine compound or the piperazine compound represented by Formula 1 and having a sulfonic acid structure or a carboxylic acid structure, a pharmaceutically acceptable salt thereof, or a derivative thereof; and donepezil, a pharmaceutically acceptable salt thereof, or a derivative thereof may be simultaneously or sequentially administered at different times with time gaps between different administrations. The administration may be two separate administrations of unit doses.

Hereinafter, the embodiments are described in greater detail. However, the embodiments are for illustrative purposes only and do not limit the scope of the present invention.

Example 1

Y-maze Behavior Test of a Mouse having Alzheimer's Disease

To test the effects of a combination of EPPS and donepezil, a Y-maze behavior test for evaluating learning memory of an Alzheimer's disease transgenic mouse was performed.

10 months old B6C3-Tg(APPswe, PSEN1dE9)85Dbo/Mmjax (The Jackson Laboratory, the U.S.A.) was used as the Alzheimer's disease transgenic mouse, as an experimental animal. The experimental animal was divided into three groups, namely, a donepezil administered group, an EPPS administered group, and a combination of donepezil and EPPS administered group were orally administered with respective drugs everyday in the amounts shown in Table 1 below and the Y-maze test was performed once every week for 13 weeks. As a control group, a transgenic mouse that was not administered with a drug was used as a negative control group and a normal mouse that was not administered with a drug was used as a positive control group.

TABLE 1

| Groups | Dosage |
| --- | --- |
| Donepezil admininstered group | Donepezil 1 mg/kg |
| EPPS administered group | EPPS 1 mg/kg |
| EPPS and donepezil administered group | Donepezil 1 mg/kg and EPPS 1 mg/kg |

The Y-maze instrument includes a maze made of a black acrylic board [branches: width 6 cm, length 40 cm, and height 12 cm] having a Y-shape in which all corners were blocked and each branch was disposed at a uniform angle of 120°. Each branch was designated as A, B, or C region, in which the experimental animal was carefully put into one branch, the experimental animal was allowed to freely move around in the Y-maze for 8 minutes, and a computer program (Ethovision 3.1, Noduls, Netherlands) was used to observe and record each branch in which the experimental animal was put into by using a camera installed on the ceiling. Frequencies and sequences of the experimental animal moving into each branch were measured to evaluate spontaneous alternation (%). Alternation of behavior was acknowledged when the experimental animal moved into three different branches (actual alternation) alternation; in other words, each movement of ABC, ACB, BAC, BCA, CAB, and CBA was recognized as an alternation and was given 1 point. When the experimental animal did not move into different branches sequentially, the movement was not given a point. % alternation rate was calculated by using a mathematical equation of [actual number of alternations/(total number of alternations−2)×100]. Also, % alternation rate was normalized based on the 100% alternation rate of the positive control group, which was the normal mouse without drug administration, and 0% alternation rate of the negative control group, which was the transgenic mouse without drug administration, and results obtained therefrom are shown in FIG. 1.

FIG. 1 shows experimental results of a Y-maze behavior of an Alzheimer's disease transgenic mouse (●: donepezil administered group, ▲: EPPS and donepezil administered group, and ■: EPPS administered group). As shown in FIG. 1, the donepezil administered group initially showed a rapid improvement in cognitive skills, but the improvement reached peak at 5 weeks and decreased at 7 weeks. Meanwhile, the EPPS administered group showed a gradual improvement in the cognitive skills compared with that of the donepezil administered group, and reached the same level of cognitive skills as the donepezil administered group at 10 weeks. The cognitive skills of the EPPS and donepezil administered group showed a gradual increase in cognitive skills compared with that of the donepezil administered group, but showed a faster increase than that of the EPPS administered group. Also, at 9 weeks, the EPPS and donepezil administered group showed the best improvement among the administered groups and showed continuous increase in the cognitive skills at 13 weeks. Also, the alternation rate of the donepezil administered group was greater than that of the EPPS and donepezil administered group at 5 weeks, and a combination of the EPPS and the donepezil was identified to be based on a pathway other than individual pathway of donepezil or EPPS.

Accordingly, donepezil showed rapid but short-term improvement in cognitive skills, and EPPS showed a long-term improvement in cognitive skills but a slower improvement compared with donepezil and a lower improvement compared with the combination of EPPS and donepezil. On the other hand, the combination of EPPS and donepezil showed better improvement in cognitive skills compared with each drug and long-term effects.

Example 2

Fear Conditioning Test of an Alzheimer's Disease Transgenic Mouse

To observe the effects of the combination of EPPS and donepezil, the experimental animal subjected to the Y-maze behavior test for 13 weeks in Example 1 was subjected to a fear conditioning test for testing fearful memory of space and sound.

The fear conditioning test was divided into a fear conditioning-contextual test that tests fearful memory of space and fear conditioning-cued test that tests fearful memory of sound.

The test included a pair of sound stimulation (CS(conditioned stimulus), 30 seconds, 85 dB, and 30 kHz) and electric shock (US(unconditioned stimulus), 1 second, and 0.5 mA), which was repeated twice. Each was performed with a term of 90 seconds and the mouse was taken out from the conditioning box 90 seconds after the last electric shock (US). The following tests were performed after 24 hours.

Contextual test: the experimental animal was maintained in the conditioning box and freeze response were measured without providing sound stimulation and electric shock, results of which were used as a scale of conditioned fearful reaction. The freeze reaction was defined as a motionless state, except for breathing.

Cued test: To change the context after 24 hours of the contextual test, the mouse was put into a box other than the box used for the contextual test and was provided with a sound stimulation identical to the contextual test (electric shock was not provided) to measure freeze reactions. The results were used as a scale for fear response conditioned to the cues.

The results the of contextual test are shown in Table 2 and FIG. 2 below and the results of the cued test are shown in Table 3 and FIG. 3 below.

TABLE 2

| | Subject of administration | | | | |
|---|---|---|---|---|---|
| | Normal mouse | Alzheimer's disease transgenic mouse | | | |
| | | Administered drug and dosage | | | |
| | Water | Water | donepezil 1 mg/kg | EPPS 1 mg/kg | EPPS 1 mg/kg and donepezil 1 mg/kg |
| Average | 51.333 | 23.739 | 16.602 | 34.437 | 38.758 |
| Standard error of the mean (SEM) | 5.821 | 5.117 | 4.218 | 2.841 | 7.672 |

TABLE 3

| | Subject of administration | | | | |
|---|---|---|---|---|---|
| | Normal mouse | Alzheimer's disease transgenic mouse | | | |
| | | Administered drug and dosage | | | |
| | Water | Water | donepezil 1 mg/kg | EPPS 1 mg/kg | EPPS 1 mg/kg and donepezil 1 mg/kg |
| Average | 71.1111 | 49.3194 | 58.9167 | 55.1042 | 64.4444 |
| Standard error of the mean (SEM) | 5.98674 | 3.33396 | 6.70921 | 5.71973 | 7.22331 |

Figure 2:
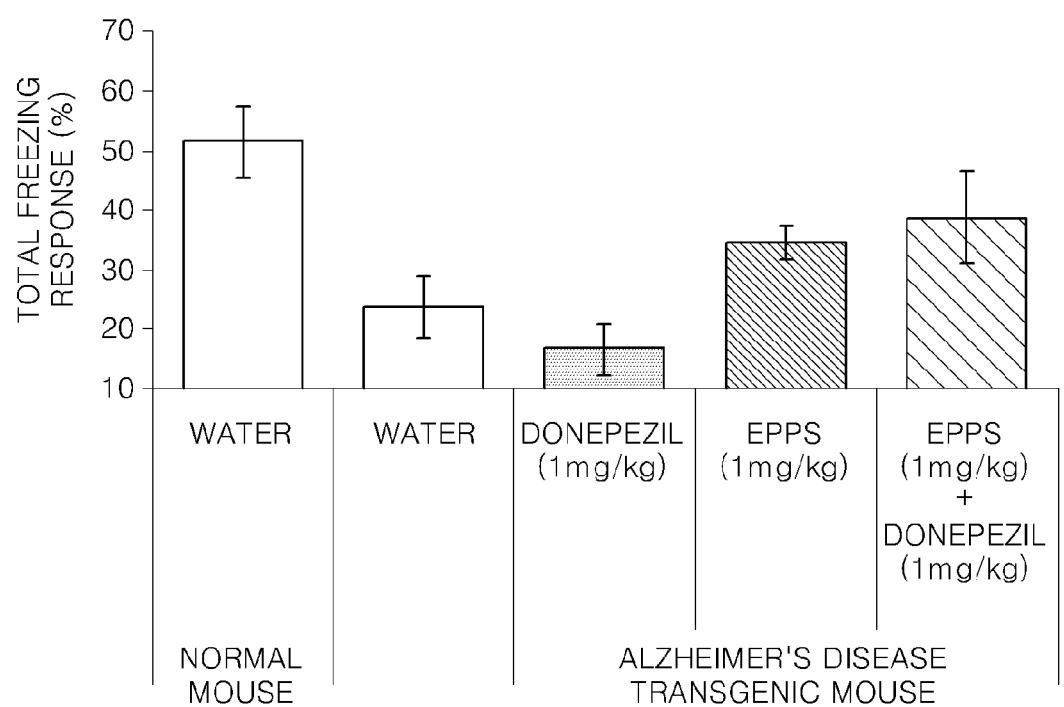
FIG. 2 shows experimental results of fear conditioning-contextual test.
Figure 3:
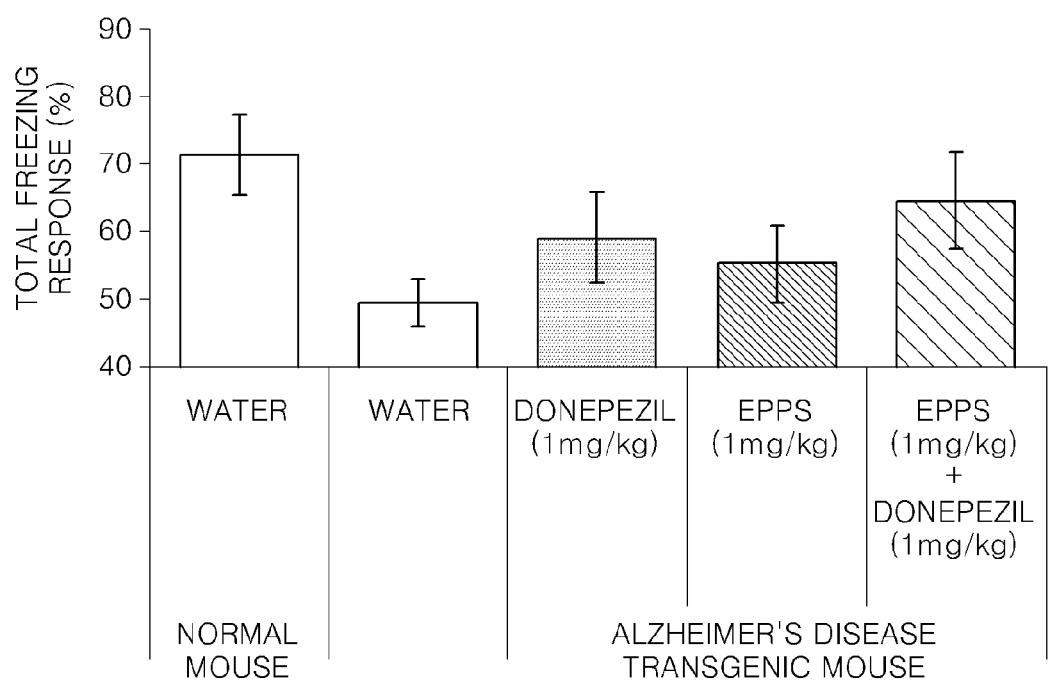
FIG. 3 shows experimental results of fear conditioning-cued test.

FIG. 2 shows experimental results of fear conditioning-contextual test and FIG. 3 shows experimental results of fear conditioning-cued test.

As shown in FIGS. 2 and 3, the EPPS and donepezil administered group showed better memory than the donepezil administered group and the EPPS administered group in the fear conditioning test for space and sound. In the contextual test that can measure effects on a hippocampus region, which is responsible for learning and memory, memory of the EPPS and donepezil administered group was substantially better than that of the donepezil administered group and the EPPS administered group. Accordingly, the combination of EPPS and donepezil showed significantly better improvement in learning and memory than EPPS and donepezil, respectively.

As described above, according to the one or more of the above embodiments of the present invention, when a pharmaceutical composition for preventing or treating cognitive impairment-related diseases, including a morpholine compound or a piperazine compound, a pharmaceutically acceptable salt thereof, or a derivative thereof; and donepezil, a pharmaceutically acceptable salt thereof, or a derivative thereof is used, accumulation of β-amyloid, which is a primary cause of dementia, may be inhibited and an amount of acetylcholine in the brain may be physiologically increased to effectively prevent or treat cognitive impairment-related diseases.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of treating a cognitive impairment-related disease selected from the list consisting of dementia, Alzheimer's disease, amnesia, or any combination thereof, the method comprising administering a morpholine compound or a piperazine compound represented by Formula 1 below and comprising a sulfonic acid structure or a carboxylic acid structure, or a pharmaceutically acceptable salt thereof; and donepezil, or a pharmaceutically acceptable salt thereof to a subject:

[Formula 1]

in Formula 1,
Z is O or N;
when Z=O, R1 is not bonded and when Z=N, R1 is —(CH2)n-OH; and
R2 is —(CH2)n-R3, n is an integer selected from 1 to 5, and R3 is —COOH or —SO3H.

2. The method of claim 1, wherein the compound represented by Formula 1 is selected from the group consisting of Formulae 1a to 1e

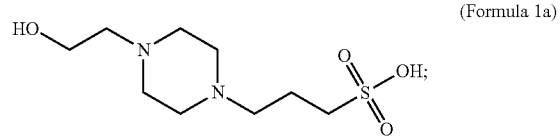
(Formula 1a)

(Formula 1b)

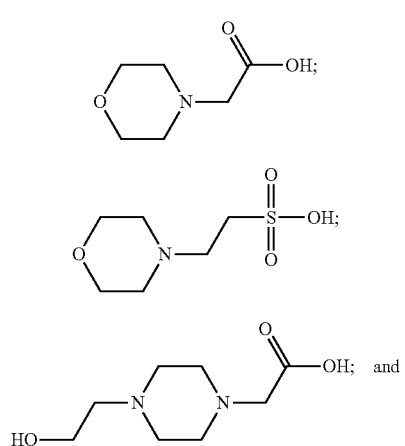

(Formula 1c)

(Formula 1d)

(Formula 1e)

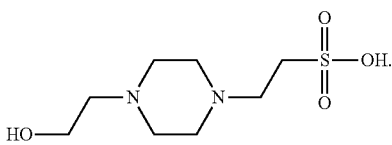

3. The method of claim 1, wherein the method comprises simultaneously or sequentially administering the morpholine compound or the piperazine compound represented by Formula 1 below and comprising the sulfonic acid structure or the carboxylic acid structure, a pharmaceutically acceptable salt thereof; and donepezil, a pharmaceutically acceptable salt thereof to a subject.

* * * * *